| United States Patent [19] | [11] Patent Number: 4,530,831 |
| Lütticken et al. | [45] Date of Patent: Jul. 23, 1985 |

[54] INFECTIOUS BURSAL DISEASE VACCINE

[75] Inventors: Heinrich D. Lütticken, Boxmeer; Daniël R. W. Cornelissen, Sambeek, both of Netherlands

[73] Assignee: Akzo N.V., Arnhem, Netherlands

[21] Appl. No.: 438,936

[22] Filed: Nov. 2, 1982

[51] Int. Cl.³ .......................... A61K 39/12; C12N 7/00
[52] U.S. Cl. ........................................ 424/89; 435/235
[58] Field of Search ............................ 424/89; 435/235

[56] References Cited

U.S. PATENT DOCUMENTS

| 3,548,055 | 12/1970 | Moulthrop | 424/89 |
| 3,769,400 | 10/1973 | Bengelsdorff | 424/89 |
| 4,357,320 | 11/1982 | Apontoweil et al. | 424/89 |

FOREIGN PATENT DOCUMENTS 143793  9/1980  Fed. Rep. of Germany ...... 435/235

OTHER PUBLICATIONS

Winterfield et al., Avian Dis 24(1): 179–188, 1980.
Cursiefen et al., Avian Pathol 8(4): 341–352, 1979.

Primary Examiner—Sidney Marantz
Assistant Examiner—Shawn P. Foley
Attorney, Agent, or Firm—Abelman Frayne Rezac & Schwab

[57] ABSTRACT

An Infectious Bursal Disease vaccine comprising the virus strain deposited at the ATCC under No. VR-2041, a process for the preparation thereof, and a method of controlling Infectious Bursal Disease of poultry by administering said vaccine.

8 Claims, No Drawings

INFECTIOUS BURSAL DISEASE VACCINE

The invention concerns a novel infectious bursal disease vaccine, a process for the preparation of live or inactivated infectious bursal disease vaccine and a novel infectious bursal disease virus strain.

The infectious bursal disease in poultry (also indicated as infectious bursitis or Gumboro disease) is known to be caused by a virus, the infectious bursal disease virus (IBDV). The poultry disease is widespread and is responsible for great economic losses. Young chickens afflicted by the disease suffer from diarrhoea, muscular hemorrhages, inflammations accompanied by bleedings, damage to the immune system and necrosis of the *Bursa fabricii*. The mortality is high and the surviving chickens show pronounced growth retardation.

The virus causing infectious bursal disease can be isolated from the *Bursa fabricii*, liver, kidneys, spleen, or other organs as well as from buffy coat of infected birds.

To control infectious bursal disease in poultry, vaccines were developed containing live or inactivated viruses propagated in chicken embryos, newborn mice, or cultures of bursal cells or chicken embryo cells.

According to the U.S. Pat. No. 3,548,055 an IBD vaccine was prepared from a disease-causing strain of the causative virus. Due to the strongly pathogenic character of these strains the viruses needed to be attenuated during at least eight consecutive passages in embryonating eggs. An even more tedious method for the preparation of an IBD vaccine was described in the U.S. Pat. No. 3,769,400. Again the preparation of the vaccine was started from a strongly pathogenic strain of the IBD virus and further proceeded through 18 to 25 serial passages in immuno-suppressed baby mice. These live vaccines, however, showed either to be too pathogenic, or to be limited in their use due to neutralization of the vaccine virus be maternally derived antibodies (MDA) present in the young chicken resulting in loss of immunizing capacity of the vaccine. These maternal antibodies are developed in hens either due to an accidental infection with infectious bursal disease virus, or due to vaccination against the disease. The antibodies are transmitted from the hens to the yolk of the developing eggs. In the developing chicken embryos these antibodies are resorbed. The maternal antibody titer in the developing chicken embryos then decreases continuously with a half-life of about 5 days. Upon vaccination of the newborn chickens the viruses thus introduced are inactivated by neutralization with these maternal antibodies. Strongly pathogenic viruses are less sensitive to this inactivation than non-pathogenic infectious bursal disease viruses. Hence, vaccines containing pathogenic viruses can be applied in an early stage after hatching, but with the drawback of a high mortality ratio or the risk of immuno suppression of the vaccinates. The vaccines containing non-pathogenic viruses can only be applied when the maternal antibody titer is sufficiently decreased, hence many weeks after hatching. This introduces a period of high risk for the chickens to be infected with infectious bursal disease. Therefore there is a strong need for a better infectious bursal disease vaccine. A novel infectious bursal disease vaccine was developed which is non-pathogenic but which is able to break through the usual level of MDA without damaging the bursa of maternally immune birds.

The novel vaccine is characterized in that it is derived from an infectious bursal disease virus strain, (Clone D78) deposited at ATCC under no. VR 2041, which is non-pathogenic for maternally immune birds and is not neutralized by the maternally derived antibodies in the majority of the birds at the recommended age of vaccination (usually 14 days post-hatching).

The IBD virus strain Clone D78 has been selected as a vaccine virus due to its immunogenic properties.

The original material used for the development of Clone D78 was a virus isolated from the bursa of fabricius of a broiler chicken and further propagated on chicken embryo fibroblast (CEF) cultures prepared from specific pathogen free (SPF) eggs. The Clone D78 was obtained by four subsequent steps of plaque purification in chicken embryo fibroblasts. Each time a well separated plaque was taken. The resulting clone, Clone D78, showed uniform plaques. The material collected from the fourth step was multiplied in chicken embryo fibroblasts. With the harvest (supernatant) 9 days incubated embryonated SPF chicken eggs were inoculated.

After incubation for 72 hours the embryos were collected and homogenized to obtain Master Seed virus. One further egg passage was made to obtain working seed. The vaccine virus is grown directly from the Working Seed.

The infectious bursal disease vaccine virus strain D78, deposited at ATCC under no. VR 2041 is by the following properties, which enable it to be identified as avian IBD virus.

1. The virus possess the nucleic acid of the type RNA; virus replication in chicken embryo fibroblast cultures was not significantly influenced by the addition of 5-fluorodesoxyuridine to the culture medium.
2. The virus is not sensitive for lipid solvents such as ether and chloroform, which is also a characteristic of avian IBD viruses.
3. Using a gel diffusion test it was demonstrated that the virus contains antigen in common with known avian IBD viruses e.g. reference strains PBG 98 and strain F 52/70. No antigens in common with other avian viruses could be detected.
4. The virus produces a cytopathic effect with plaque formation if cell cultures are overlaid with agar medium. Results of virus neutralization tests (plaque reduction tests) show that the virus is only neutralized by specific antisera raised against IBD viruses and that the virus is unrelated to other avian viruses, e.g. Adeno, Marek's, Reo, Rota, Pox, Leucosis, AE (Avian Encephalitis), IB (Infectious Bronchitis) and ND (New Castle Disease) viruses.
5. According to the nomenclature for Avian IBD viruses proposed by McFerran* the virus belongs to the serotype 1 for which strain PBG 98 is proposed as a reference strain.
6. After vaccination of SPF chickens or antibody free turkeys with live or inactivated antigen of strain D78, the birds respond with precipitating and type specific neutralizing antibodies and they are immune to a subsequent infection with IBD strains of the same serotype.

*Mc Ferran, J. B. et al. (1980). Isolation and serological studies with infectious bursal disease viruses from fowl, turkeys and ducks. Demonstration of a second serotype. Avian Pathology 9, 395–404

The virus can be grown in embryonated SPF chicken eggs or in cell culture preferably from avian tissues. To prepare a live vaccine tissue culture fluids and/or cells are harvested. In the case of embryonated eggs the embryos and/or the membranes and/or the allantoic fluids are harvested. Due to the non-pathogenic character of strain D78 no further adaptation or attenuation of the strain is required to prepare a live vaccine.

The preparation of a live vaccine is carried out in a manner known per se.

Live vaccines may be administered by eye drop, nose drop, drinking water, spray methods or injection at an age varying from two weeks old to ten weeks old. Antibody free birds should preferably be vaccinated at 6–10 weeks of age.

For live vaccines a dosage may be used in a range of log 3 to log 7 $TCID_{50}$ ($TCID$ = tissue culture infective dose) or log 3 to log 7 pfu (plaque forming units) per bird preferably between log 4 and log 5 pfu.

Live vaccines containing Clone D78 are suitable for the vaccination of broiler chickens to be protected against field challenge with virulent IBD viruses and for the vaccination of future breeders and layers to protect the birds against field challenge and/or to provide a basic immunity (priming) for a subsequent vaccination with inactivated IBD vaccines. Clone D78 can also be used to prepare an inactivated vaccine. Clone D78 retains its immunogenicity vaccine. Clone D78 retains its immunogenicity after inactivation.

To prepare an inactivated vaccine from D78 the harvested embryos or tissue culture fluid may be inactivated by e.g. formaldehyde or β-propiolactone. After inactivation and, if necessary, adjusting the pH and neutralizing the inactivating agent, the inactivated antigen may be mixed with an adjuvant. The adjuvant can be for example aluminium hydroxide or a composition consisting of mineral oil or a plant oil and one or more emulsifiers like Tween 80 and Span 80.

Inactivated vaccines may contain the antigenic equivalent of log 5 to log 8 $TCID_{50}$ per bird dose preferably between log 6 and log 8 $TCID_{50}$ or 6–8 log pfu. Combinations of inactivated D78 antigen with one or more unrelated avian viruses (in particular New Castle Disease virus, Infectious Bronchitis virus, Reo virus and Adeno virus) in inactivated vaccines is also part of this invention. The inactivated antigens can be emulsified to a water-oil emulsion as described in Example IV. In case of combined vaccines inactivated antigens can be added to the IBD antigenic phase in a dosage which fulfills the requirements for inactivated vaccines according to CFR 9, 113–120, in particular in the case of combined vaccines with NOV the requirements of CFR 9, 113–125. Inactivated vaccines will usually be given at an age of 10–20 weeks by subcutaneous or intramuscular injection.

EXAMPLE I

Safety and Innocuity

Administration of Clone D78 to SPF chickens.

12 SPF white Leghorn chickens, 6 weeks of age were live vaccinated with log 5 pfu per bird. Birds were killed 12 days p.v. and bursae examined for histological lesions. The birds showed no clinical signs of disease after administration of the vaccine. Macroscopically no influence of the vaccine virus on bursa size could be observed. Microscopically bursa lesions which, however, were not typical for IBD were detectable in the following degrees:

3×25% depletion + histiocytes
8×50–70% depletion
1×75% depletion.

12 Hatchmates of the birds vaccinated with a live commercially available vaccine (Delvax) showed marked bursa lesions (90% depletion in 12/12 birds), typical for IBD.

It can be concluded that vaccination with live D78 vaccine does not cause bursa lesions other than slight and transient depletion which can also be seen after vaccination with live vaccines not containing IBDV.

Immunosuppression test

The damage of the bursa by an IBDV field virus can result in immunosuppression, which is more pronounced in young chickens. To investigate whether the slight to moderate bursa damage IBD virus strain D78 caused in SPF chickens can influence the ability of birds to react adequate on a subsequent vaccination with a different antigen, an immunosuppression experiment was carried out as follows.

SPF birds vaccinated at day-old with 4.0 log pfu Clone D78 or 10 $CID_{50}$ of the pathogenic IBDV strain F 52/70 respectively, 14 days later eye drop vaccination with 4.0 log $EID_{50}$ of the NDV vaccine strain Clone 30, at 28 days of age birds were subjected to a NDV challenge infection with the virulent NDV strain Herts. Results are shown in Table 1.

TABLE 1

| | Influence of early IBDV infection on the protection rate against NDV challenge. | | |
|---|---|---|---|
| Group | IBD virus at day-old | ND vaccine at day 14 | Protection against challenge at day 28 no. protected/tested |
| 1 | none | no | 0/25 |
| 2 | none | yes | 24/24 |
| 3 | F 52/70 | yes | 12/23 |
| 4 | Clone D78 | yes | 25/25 |

Thus it can be concluded that administration of Clone D78 to susceptible day-old chicks had in contrast to administration of pathogenic IBDV no negative influence on the ability of the birds to respond on a live ND vaccination, measured by resistance to challenge infection.

Lack of reversion to virulence

Live vaccine viruses spread from bird to bird when used under field conditions. It is desirable to prove that the degree of residual pathogenicity of a vaccine virus strain once being established as acceptable does not change during passages of the virus from bird to bird.

The vaccine virus has been passaged in SPF birds. Starting with a commercial vaccine batch (no. 9015c) 7 passages have been made by contact transmission in isolators. The birds from the seventh passage have been killed and the virus was re-isolated from the bursa and spleen on CEF. The re-isolated vaccine virus (after seven bird passages and one tissue culture passage) has been administered to SPF birds in a safety test and an immunosuppression test.

Safety test of bird passaged virus strain D78.

Two groups of each 20 SPF chickens vaccinated at day-old with the vaccine passage level resp. the bird passage material. 21 Days p.i. bursae of the birds were histologically examined. In both groups 20/20 birds showed lymphoid depletion of the same degree as observed in earlier experiments with D78 seed material and different vaccine batches. No difference could be seen in the severity of the bursa lesions caused by the vaccine and the bird passage material respectively.

Immunosuppression test of bird passaged virus strain D78.

The bird passage material and the vaccine passage level had after application to susceptible chicks no adverse effect on the immune response to a live Newcastle Disease Vaccine.

From these safety—innocuity experiments it appears that Clone D78 causes a histologically demonstrable lymphocyte depletion in SPF birds. However, the administration of D78 to day-old SPF birds did not result in an immunosuppression. When administered to antibody positive birds at the recommended age of 14 days no adverse influence of the vaccine virus could be detected (see also under efficacy tests).

EXAMPLE II

Efficacy of live vaccine (laboratory experiments)

Vaccination with Clone D78 results in a precipitating and a neutralizing antibody response. It has been shown that neutralizing antibody response is correlated with protection. In addition to the antibody response, protection can also be measured by histological examination of the bursa after a challenge infection. The bursal damage caused by the Clone D78 vaccine virus does—in contrast to many more pathogenic vaccine strains—not preclude histological examination of the bursae of vaccinated chickens as parameter for protection.

Take of strain D78 in SPF chickens (antibody negative to IBD).

Clone D78 live vaccine was administered in graded doses to 14 day-old SPF chickens by eye drop and by oral instillation. Serological response has been tested at 14 and 28 days p.v. (for precipitating antibody (AGP=agar gel precipitation) and neutralizing antibody (VN=virus neutralization)).

TABLE 2

| Vaccine dose | No. of birds pos./tested | | | |
|---|---|---|---|---|
| | Day 14 p.v. | | Day 28 p.v. | |
| | AGP | VN | AGP | VN |
| orally | | | | |
| 100 pfu | 7/12 | 8/11 | 12/12 | 12/12 |
| 1,000 pfu | 15/15 | 15/15 | 15/15 | 15/15 |
| 10,000 pfu | 12/12 | 12/12 | 12/12 | 12/12 |
| eye drop | | | | |
| 100 pfu | 0/12 | 0/12 | /12 | 0/12 |
| 1,000 pfu | 12/13 | 12/13 | 12/13 | 12/13 |
| 10,000 pfu | 11/11 | 11/11 | 12/12 | 12/12 |

From the results (shown in Table 2) it can be concluded that a minimum bird dose of $10^3$ pfu is required to achieve virus replication in antibody free birds.

Take of strain D78 in chickens with maternally derived antibodies. As mentioned before, Clone D78 is unique in that it can break through certain level of MDA without damaging the bursa of maternally immune birds.

Antibody response of MDA positive chickens

Two groups of each 15 one day old commercial broiler chickens, all having maternally derived antibody titers of 1:2048 were placed in isolators. One group was vaccinated at 14 days of age with 4.0 log pfu by oculonasal instillation of live vaccine at the master seed passage level. The other group was kept as a control. At 28, 35 and 42 days of age both groups were controlled for precipitating antibody response (using the Ouchterlony technique) and for virus neutralizing antibody titer (using the plaque reduction test). The neutralizing antibody titer represents the highest serum dilution which gives a 90% reduction of D78 virus plaques. In table 3 are indicated the numbers of chickens in each group (vaccinates and controls) with their respective antibody titers, and the precipitating antibody response in both groups, at the various days of age.

It can be concluded that Clone D78 is able to induce an active immune response in 10 out of 12 antibody positive birds when administered at 14 days of age. The two none responders, both had a MDA neutralizing titer of $\geq 1:256$ at time of vaccination. In a series of similar experiments it could be confirmed that take of the D78 live vaccine cannot be expected in birds with MDA titers $> 1:256$.

TABLE 3

| days of age | Control group | | | | | Vaccinated group | | | | |
|---|---|---|---|---|---|---|---|---|---|---|
| | 0 | 14 | 28 | 35 | 42 | 0 | 14 | 28 | 35 | 42 |
| precipitating antibody response (no pos.) | 15 | 0 | 0 | 0 | 0 | 15 | 0 | 9 | 10 | 10 |
| no. with neutralizing antibody titer | | | | | | | | | | |
| 1:2048 | 15 | | | | | 15 | | | 5 | 5 |
| 1024 | | | | | | | | 2 | 4 | 5 |
| 512 | | | | | | | | | | |
| 256 | | 2 | | | | | 2 | 4 | | |
| 128 | | 2 | | | | | 1 | 2 | | |
| 64 | | 2 | 1 | | | | 2 | 2 | 1 | 1 |
| 32 | | 3 | 2 | 1 | | | 4 | 2 | 2 | 1 |
| 16 | | 2 | 3 | 1 | | | 2 | | | |
| lower than 1:16 | | 4 | 8 | 9 | 11 | | 1 | | | |
| total no. chicks | 15 | 15 | 14 | 11 | 11 | 15 | 12 | 12 | 12 | 12 |

Protection of vaccinated birds against challenge

A comparative experiment using SPF birds and MDA positive broiler chickens has been carried out to demonstrate the protective effect of D78 live vaccine against a severe experimental challenge infection. Birds housed in isolators were vaccinated at 14 days of age with 4.0 log pfu/bird and were challenged at 21 and 28 days respectively with 1.9 $TCID_{50}$ of the virulent IBDV strain F 52/70.

11 Days after challenge the vaccinated and the surviving control birds were killed and their bursae examined for IBDV lesions due to the challenge infection. Results shown in Table 4, clearly indicate that vaccination of antibody free and MDA positive chickens with live Clone D78 vaccine as early as 14 days of age gives an excellent protection against a severe artificial challenge.

TABLE 4

Antibody response (plaque reduction test) and protection rate of SPF and MDA positive chickens, vaccinated with live D78 vaccine at 14 days of age and challenged at 21 or 28 days of age.

| Group | Day of challenge | no. of birds protected tested | no. of birds with Seroconversion at day of challenge tested |
|---|---|---|---|
| controls SPF | 21 | 0/10 | 0/10 |
| Vaccinates SPF | 21 | 10/10 | 10/10 |
| Vaccinates SPF | 28 | 10/10 | 10/10 |
| Controls MDA positive | 21 | 2/9 | n.d. |
| Vaccinates MDA positive | 21 | 7/10 | n.d. |
| Controls MDA positive | 28 | 0/10 | 0/10 |
| Vaccinates MDA positive | 28 | 10/10 | 8/10 |

EXAMPLE III

Live Vaccine

Propagation of the virus in SPF eggs

Embryonated SPF chicken eggs (9–11 days incubated) are inoculated with log 3 to log 5 pfu per egg of seed virus in the allantoic cavity or on the allantoic membrane. The eggs are candled 18-24 hours p.i. and aspecific died embryos are discarded. After an incubation period of 48-96 hours whole embryos and/or AAF are harvested, homogenized and clarified by centrifugation or filtration. To achieve an optimal virus extraction from the embryo tissues a suitable wetting agent (e.g. Tween 80) and/or an enzyme (e.g. Trypsin) may be added to the embryo homogenate. When indicated antibiotics can be added to the harvest.

Propagation of the virus in cell culture

Preferable method: confluent monolayers of chicken embryo fibroblast are infected with the seed virus at a MOI between 1 and 0.001. 24-48 Hours p.i. when 80-100% CPE is visible, supernatant with or without cells is harvested, clarified by centrifugation, treated with wetting agents and/or enzymes when indicated. Alternative method are:
1. Multilayer technique with CEF on roller bottles;
2. Propagation of the virus on CEF attached to microcarriers;
3. Propagation of the virus on permanent cellines (e.g. verocells) either in suspension or on stationary cultures.

Preparation of the vaccine

The virus harvest can subsequently be processed to a pharmaceutical preparation by methods known per se. Stabilizing can be carried out by addition of a suitable stabilizing agent such as an albumin, casein, or suitable mixtures. The bulk harvest can be frozen down at temperatures lower than −35° C. and stored until further treatment. Alternatively the bulk is stored at +4° C. until further treatment. Samples are taken to assay the virus content. Stabilized virus harvest (after thawing when the material was frozen) is filled into lyophilization vials in 1-2 ml quantities. The virus content is adjusted in such a way that the titer after freezedrying is at least 4.0 log pfu per bird dose. The vials are sealed under vacuum or under nitrogen after freezedrying.

EXAMPLE IV

Inactivated vaccine

Preparation of the virus

The virus is propagated as described under storage of the bulk in the preparation of live vaccines prior to inactivation and further processing can be done at temperatures lower than −35° C.

Inactivation of the virus

The frozen harvest is thawed, a sample is taken to determine the virus titer; the AAF is inactivated by addition of formaline to a final concentration of 0.4%. After 24 hours at room temperature the formaline can be neutralized by sodium metabisulphite. A sample is tested for inactivation by inoculating in susceptible SPF chicken embryos or on CEF cultures with at least one passage. Alternative methods for inactivation are the use of β-propiolactone, ethylene-imine or derivatives thereof.

The inactivated harvest is diluted or concentrated depending on the titer requirements. Concentration can also be done prior to inactivation. Suitable methods are ultrafiltration or concentration by polyethyleneglycol precipitation. Inactivated antigen can be stored at +4° C.

Preparation of vaccine

To prepare an inactivated oil emulsion vaccine, Tween® 80 is added at a concentration of 3.5% to the inactivated antigen suspension. The antigenic content is adjusted to at least 6.0 log pfu per bird dose. The antigenic mass can be determined by an enzyme immuno assay. The suspension is subsequently emulsified into the oil phase of the adjuvant in the ratio of oil to water of 70:30 or 55:45. The composition of the adjuvent is:

Marcol®: 52:90%
Tween®: 80:3.5%
Span®: 80:6.5%

The average particle size of the aqueous phase is less than 3.0 μm.

EXAMPLE V

Use of live vaccine containing Clone D78 in the field

The direct losses from mortality are not the most important effect of Gumboro Disease in the poultry management. The economical results are much more influenced by its indirect effects, which are already induced by subclinical forms of Gumboro Disease. The indirect effects are manifested as retarded growth, bad food conversion and increased susceptibility to infectious diseases.

Therefore, the field trials with the IBD vaccine strain D78 were monitored by the following parameters:

Mortality
Time needed for fattening
Mean chicken weight at the time of slaughter
Food conversion rate
EPEF
Administration of curative medications.

The EPEF is the European Production Efficiency Factor (EPEF) and is defined according to Voeten and Brus (The production number as a criterion for the breeding results of broiler chickens (in Dutch with a summary in English, French and German). Tijdschrift voor Dierengeneeskunde 91, 1233–1239 (1966)) as $$EPEF = \frac{\text{Percent survivors} \times \text{Grams of growth per day}}{10 \times \text{Feed conversion ratio}}$$

The EPEF is especially well suited for the comparison of economical results in broiler chicken management, because it summarizes the combined influences of mortality, growth and feed conversion.

A total number of 38 Spanish broiler flocks was used in this study. These flocks fall in three different groups:

I. Vaccinated with Clone D78
II. Vaccinated with live IBD vaccine manufactured by Duphar B. V., Weesp, Holland. Dosage administration of this vaccine was done according to the manufacturer's instructions.
III. Not vaccinated against Infections Bursal Diseases.

The numbers of flocks in each group, the numbers of chickens involved and the summarized production figures are presented in Table 5.

The cost of curative medications could not be obtained for all flocks in these trails. The total cost per group for the flocks from which medication data were available are shown in Table 6. As these trials were performed in Spain, the cost is expressed in Pesetas.

From the detailed data per flock the production numbers (EPEF's) are shown in Table 7.

In all respects the mean results were better in group I flocks vaccinated with Clone D78:

lowest mortality,
shortest holding time, together with
highest chicken weight and, therefore,
highest growth rate; together with lowest feed conversion rate, gives
superior production number (EPEF),
minimal cost of curative medication.

Moreover, the standard deviation of the production numbers was smallest in the Clone D78 group. This indicated relatively little differences between production results per flock. Correspondingly, in groups II and III some flocks had a very low production number; although there were more flocks in group I, no very low production numbers occurred in that group.

Broiler flocks vaccinated with Gumboro live IBD Vaccine strain D78 had better production economy than flocks vaccinated with a different Gumboro vaccine or not vaccinated against Gumboro Disease.

TABLE 5

Summary of the results of field trials with IBD vaccine strain D78

| Group | Vaccine | Number of flocks | Number of chickens placed | Number of chickens delivered | Percent mortality | Holding time (days) | Meat weight (kg) | Chicken weight (kg) | Feed consumption (kg) | Feed conversion rate (kg/kg) | Chicken growth rate (g/day) | EPEF |
|---|---|---|---|---|---|---|---|---|---|---|---|---|
| I | Clone D78 | 16 | 171609 | 161936 | 5.64 | 53.6 | 300727 | 1.859 | 642460 | 2.136 | 34.7 | 153 |
| II | Other | 14 | 174156 | 162512 | 6.69 | 55.2 | 293940 | 1.809 | 647700 | 2.204 | 32.8 | 139 |
| III | Unvaccinated | 8 | 140836 | 129912 | 7.75 | 55.1 | 239229 | 1.841 | 535450 | 2.238 | 33.4 | 138 |

TABLE 6

Cost of curative medications in field trials with IBD vaccine strain D78

| Group | Vaccine | Number of flocks | Number of chickens | Cost of curative medication (Pesetas) Total | per chicken |
|---|---|---|---|---|---|
| I | Clone D78 | 14 | 147,120 | 374,049 | 2.54 |
| II | Other | 10 | 95,616 | 259,044 | 2.71 |
| III | Unvaccinated | 5 | 84,336 | 264,050 | 3.13 |

TABLE 7

Production numbers (EPEF's) for each flock in the field trials with IBD vaccine strain D78

| Group Vaccine | I Clone D78 | II Other | III Unvaccinated |
|---|---|---|---|
| Mean | 154.45 | 141.98 | 146.47 |
| Standard Deviation | 10.19 | 15.70 | 19.73 |

EXAMPLE VI

Vaccination of turkeys with live D78 vaccine in the field

A flock of turkey breeders, 6,300 hens and 700 males were vaccinated at 21 days of age with 4.3 log pfu of IBD vaccine Clone D78. Birds were bled 14 and 56 days p.v. for antibody testing using agar gel precipitation (AGP) and virus neutralizing antibody titer determination (VN titer).

No adverse reaction could be observed, the vaccinated birds developed as healthy as hatchmates housed in a different farm. From the serological response shown in Table 8 it can be concluded that turkey breeders respond to a live D78 vaccination with neutralizing antibodies of a level known to be protective.

TABLE 8

IBDV antibody response after vaccination with live D78 vaccine

| | AGP pos./tested | Number sera with a VN titer of (2 log) | | | | | | | | | | | | | | | | | | | | | $\phi$ |
|---|---|---|---|---|---|---|---|---|---|---|---|---|---|---|---|---|---|---|---|---|---|---|---|
| | | <4 | 4 | 4.5 | 5 | 5.5 | 6 | 6.5 | <7 | 7 | 7.5 | 8 | 8.5 | 9 | 9.5 | 10 | 10.5 | 11 | 11.5 | 12 | 12.5 | >14 | |
| prior to vacc. | 0/30 | 26 | 3 | 1 | | | | | | | | | | | | | | | | | | | <4.02 ± 0.09 |
| 14 days p.v. | 27/30 | | 2 | 1 | | | 1 | 1 | | 4 | 1 | 4 | 5 | 7 | 1 | 1 | | 2 | | | | | 7.98 ± 1.73 |
| 56 days p.v. | 30/30 | | | | 1 | | 2 | | | 1 | 1 | 2 | 1 | 5 | | 4 | 4 | 1 | 3 | 1 | 2 | 2 | 9.78 ± 2.22 |

Production numbers (EPEF's) for each flock in the field trials with IBD vaccine strain D78

| Group Vaccine | I Clone D78 | II Other | III Unvaccinated |
|---|---|---|---|
| Flock no. | | | |
| 1 | 162.04 | 152.77 | 145.90 |
| 2 | 157.33 | 162.32 | 165.13 |
| 3 | 153.67 | 155.35 | 161.31 |
| 4 | 161.75 | 155.74 | 161.67 |
| 5 | 168.81 | 155.81 | 138.34 |
| 6 | 157.15 | 132.62 | 108.75 |
| 7 | 164.73 | 156.00 | 160.03 |
| 8 | 138.89 | 131.08 | 130.59 |
| 9 | 153.39 | 124.95 | — |
| 10 | 149.11 | 136.66 | — |
| 11 | 160.58 | 152.46 | — |
| 12 | 161.06 | 123.40 | — |
| 13 | 134.62 | 111.75 | — |
| 14 | 159.32 | 136.84 | — |
| 15 | 135.86 | — | — |
| 16 | 152.84 | — | — |

We claim:

1. A live vaccine effective against Infectious Bursal Disease in poultry upon a single administration to birds at usual age of vaccination Infectious Bursal Disease virus belonging to the strain deposited at the ATCC under No. VR-2041.

2. An inactivated vaccine effective against Infectious Bursal Disease in poultry upon a administration to birds at the usual age of vaccination comprising an inactivated Infectious Bursal Disease virus belonging to the deposited in the ATCC under No. VR-2041.

3. An inactivated vaccine according to claim 2 further containing one or more live or inactivated viruses of the group consisting of New Castle Disease virus, Infectious Bronchitis virus, Reo virus and Adeno virus.

4. A virus suspension containing the Infectious Bursal Disease virus deposited at ATCC under no. VR-2041.

5. A lyophilized virus composition containing the Infectious Bursal Disease virus deposited at ATCC under no. VR-2041.

6. A method of controlling Infectious Bursal Disease of poultry which a single administration of vaccine containing an Infectious Bursal Disease virus of the strain deposited in the ATCC under No. VR-2041 to birds at the usual age of vaccination.

7. In a method for the preparation of a live vaccine that protects poultry against Infectious Bursal Disease which comprises:
  a. growing an Infectious Bursal Disease virus on a culture medium selected from the group consisting of embryonated eggs, chicken embryo cells, a culture of bursal cells and newborn mice,
  b. subsequently arresting the cultivated virus material, and
  c. subjecting the material obtained from step b. to at least one of the following treatments:
    i. clarifying by centrifugation and/or filtration;
    ii. adding a stabilizing agent;
    iii. putting the material in a vessel;
    iv. freeze-drying, the improvement comprising that the Infectious Bursal Disease virus grown in step a. is the virus of the strain deposited in the ATCC under No. VR-2041.

8. In a method for the preparation of an inactivated vaccine that protects poultry against Infectious Bursal Disease which comprises:
  a. growing an Infectious Bursal Disease virus on a culture medium selected from the group consisting of embryonated eggs, chicken embryo cells, a culture of bursal cells and newborn mice,
  b. subsequently harvesting the cultivated virus material obtained under step a.,
  c. inactivating the harvested material, and
  d. subjecting the inactivated material to at least one of the following treatments:
    i. clarifying by centrifugation and/or filtration;
    ii. adding a stabilizing agent;
    iii. adding acid or base to adjust the pH;
    iv. adding adjuvant;
    v. adding emulsifier, the improvement comprising that the Infectious Bursal Disease virus grown in step a. is the virus of the strain deposited in ATCC under No. VR-2041.

* * * * *

UNITED STATES PATENT AND TRADEMARK OFFICE
CERTIFICATE OF CORRECTION

PATENT NO. : 4,530,831

DATED : July 23, 1985

INVENTOR(S) : Heinrich D. Lutticken and Daniel R. W. Cornelissen

It is certified that error appears in the above-identified patent and that said Letters Patent are hereby corrected as shown below:

Column 10, line 55, after "at" insert -- the --

Column 10, line 55, after "vaccination" insert -- comprising a live --

Column 10, line 61, after "belonging to the" insert -- strain --

Signed and Sealed this

Eleventh Day of November, 1986

Attest:

DONALD J. QUIGG

Attesting Officer

Commissioner of Patents and Trademarks